United States Patent [19]

Hayashi

[11] Patent Number: 4,837,603
[45] Date of Patent: Jun. 6, 1989

[54] METHOD OF CORRECTING AZIMUTH ANGLE OF PHOTOMETRIC ELLIPSOMETERS

[75] Inventor: Yasuaki Hayashi, Kanagawa, Japan

[73] Assignee: Nihon Shinku Gijutsu Kabushiki Kaisha, Kanagawa, Japan

[21] Appl. No.: 925,102

[22] Filed: Oct. 29, 1986

[30] Foreign Application Priority Data

Apr. 11, 1986 [JP] Japan .................................. 61-82327

[51] Int. Cl.⁴ ............................................... G01J 4/00
[52] U.S. Cl. ...................................................... 356/369
[58] Field of Search ................................ 356/369, 364

[56] References Cited

U.S. PATENT DOCUMENTS 4,585,348  4/1986  Chastang et al. .................... 356/369

OTHER PUBLICATIONS

K. Riedling, "Evaluation of Adjustment Data for Simple Ellipsometers", Thin Solid Films, 61(1979), Aug. 15, 1979, Institut fuer Elektrotechnik Technische Universitaet Wien.

Primary Examiner—Gene Wan
Attorney, Agent, or Firm—Mason, Fenwick & Lawrence

[57] ABSTRACT

Method of correcting the azimuth angle of a photometric ellipsometer in which accurate ellipsometric parameters $\Psi$ and $\Delta$ can be simply and readily obtained by measuring by means of a suitable method the errors in the azimuth angle of a polarizer assembly or a polarizer and an analyzer system or an analyzer and subtracting the error value from the actually measured value.

4 Claims, 1 Drawing Sheet

METHOD OF CORRECTING AZIMUTH ANGLE OF PHOTOMETRIC ELLIPSOMETERS

FIELD OF THE INVENTION

The present invention relates to a method of correcting the azimuth angle of a photometric ellipsometer which may be used as a process monitor for evaluating, for example, a thin film to be produced in a processor.

BACKGROUND OF THE INVENTION

Since the evaluation of a thin film by ellipsometry can be utilized simultaneously to measure both the thickness and the refractive index of the file with extreme accuracy, it has various applications. For example, a monitoring method which utilizes ellipsometry in a process for forming a thin film can accurately evaluate the thickness and the composition of the film and thus has been performing an effective role in various recent semiconductor manufacturing processes required for strict accuracy. Some conventional methods of monitoring a thin film utilizing the ellipsometry are disclosed in Japanese Patent Publication Nos. 42944/74, 22912/75 and 46825/77.

The evaluation of a thin film by the ellipsometry method has been conventionally conducted heretofore after the thin film was formed on a substrate. It will be appreciated that if the ellipsometer is to be used as an in-process monitor, the thin film forming can be accurately controlled and then the effectiveness thereof may be increased. However, the ellipsometer is not yet utilized at least industrially as an in-process monitor at present. This is because the adjustment of an optical system is also difficult to associate the ellipsometer in a processor and hence an error feasibly occurs.

More specifically, in such a case, a sample holder disposed oppositely to an RF electrode in a vacuum chamber of the processor is used as a sample base for a sample to be evaluated, and a polarizer assembly and analyzer system are mounted at the position remote from the sample holder in the vacuum chamber, i.e., outside the chamber, with the result that the settlement of an incident angle and an azimuth angle (rotating angle around an optical axis) is not ready as the conventional integral ellipsometer. Consequently, when the ellipsometer is utilized by associating as a process monitor in the processor, it has such disadvantages that the adjustment of the azimuth angle is very difficult and its accuracy is wrong lack of practical utility.

Therefore, the present invention has for its object to provide a method of correcting the azimuth angle of a photometric ellipsometer capable of reducing the error of the azimuth angle by a simple way as low as possible to overcome the above-mentioned disadvantages.

SUMMARY OF THE INVENTION

According to one aspect of the present invention, there is provided a method of correcting the azimuth angle of a photometric ellipsometer in which a quarter-wave plate is disposed at an azimuth angle of 45° to a polarizer assembly or an analyzer system, comprising the steps of positioning a polarizer or an analyzer with an azimuth angle by 45° each time, measuring ellipsometric parameters $\Psi'$ and $\Delta'$, and determining the errors in the azimuth angle of the polarizer assembly or polarizer and the azimuth angle of the analyzer system or analyzer.

According to a second aspect of the present invention, there is provided a method of correcting the azimuth angle of a photometric ellipsometer in which a quarter-wave plate is disposed at an azimuth angle of 45° to a polarizer assembly or an analyzer system, comprising the steps of positioning a polarizer or an analyzer with an azimuth angle by 45° each time, measuring ellipsometric parameters $\Psi'$ and $\Delta'$, and cancelling the errors in the azimuth angle of the polarizer assembly or polarizer and the analyzer system or analyzer from the measured ellipsometric parametess $\Psi'$ and $\Delta'$ to obtain accurate ellipsometric parametsrs $\Psi$ and $\Delta$.

The accurate ellipsometric parametsrs $\Psi$ and $\Delta$ may be obtained by the following equation:

$$\Psi = \Psi' + \sin 2\Psi' \cdot \sin 2P \cdot \delta P - \sin(\Delta' + 2P) \cdot \delta A$$

$$\Delta = \Delta' - \frac{2\cos(\Delta' + 2P)}{\tan 2\Psi'} \cdot \delta A$$

wherein P represents the azimuth angle of the polarizer or analyzer and $\delta P$ and $\delta A$ represent the errors in the azimuth angles of the polarizer or analyzer and the analyzer or polarizer, respectively.

According to a third aspect of the present invention, there is provided a method of correcting the azimuth angle of a photometric ellipsometer in which a quarter-wave plate is disposed at an azimuth angle of 45° to a polarizer assembly or an analyzer system, comprising the steps of positioning a polarizer or an analyzer with an azimuth angle by 45° each time, measuring ellipsometric parameters $\Psi'$ and $\Delta'$, and summing the values of the measured ellipsometric parameters $\Psi'$ and $\Delta'$ to cancel the error in the azimuth angles of the polarizer assembly or polarizer and the analyzer system or analyzer thereby obtain accurate ellipsometric parameters $\Psi$ and $\Delta$.

The accurate ellipsometric parameters $\Psi$ and $\Delta$ may be obtained by the following equation:

$$\Psi = \frac{\Psi'_{45} + \Psi'_{135}}{2} \quad \Delta = \frac{\Delta'_0 + \Delta'_{90}}{2}$$

when the azimuth angle P of the polarizer or analyzer is set to 0°, 45°, 90° and 135°.

According to a fourth aspect of the present invention, there is provided a method of correcting the azimuth angle of a photometric ellipsometer in which a quarter-wave plate is disposed at an azimuth angle of 45° to a polarizer assembly or an analyzer system, comprising the step of measuring a difference between the azimuth angle of a polarizer or an analyzer and the azimuth angle of said quarter-wave plate when the quarter-wave plate is positioned at the azimuth angles 45° and 135°.

According to a fifth aspect of the present invention, there is provided a method of correcting the azimuth angle of a photometric ellipsometer in which a quarter-wave plate is disposed at an azimuth angle of 45° to a polarizer assembly or an analyzer system, comprising the step of integrating a polarizer or an analyzer with the quarterwave plate to adjust the azimuth angle.

BRIEF DESCRIPTION OF THE DRAWINGS

The invention will be described in detail with reference to the accompany drawings.

DETAILED DESCRIPTION

Figure 1:
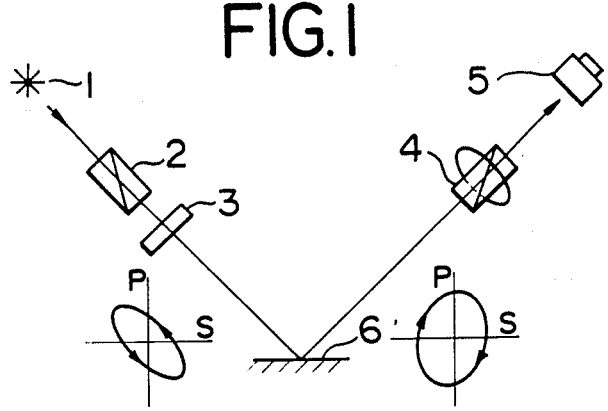
FIG. 1 is a schematic diagram showing an embodiment of the present invention.

In FIG. 1 there is shown an embodiment according to the present invention which is carried out as a rotatinganalyzer type ellipsometric monitor in which a quarter-wave plate is disposed on a polarizer assembly. The apparatus comprises a light source 1, a polarizer 2 having an azimuth angle P, a quarter-wave plate 3 with an azimuth angle of 45°, an analyzer 4 having an azimuth angle A and a photodetector 5. Reference numeral 6 designates a sample or specimen to be evaluated.

In the illustrated apparatus, the actual ellipsometric parameters $\Psi$ and $\Delta$ have as linear approximate equations the following relationships to the measured ellipsometric parameters $\Psi'$ and $\Delta'$.

$$\left. \begin{array}{l} \Psi = \Psi' + \sin2\Psi' \cdot \sin2P \cdot \delta C - \sin(\Delta' + 2P) \cdot \delta A \\ \Delta = \Delta' - 2\delta P + 2\delta C - \frac{2\cos(\Delta' + 2P)}{\tan2\Psi'} \cdot \delta A \end{array} \right\} \quad (1)$$

wherein $\delta P$, $\delta C$ and $\delta A$ are the errors of the azimuth angles of the polarizer 2, the quarter-wave plate 3 and the analyzer 4, respectively, and P is the azimuth angle of the polarizer 2 which may be obtained as below. The intensity I of the light beam incident to the analyzer 4 has the following relationship as the function of the azimuth angle A thereof.

$$I = I_0(1 + a \cdot \cos2A + b \cdot \sin2A) \quad (2)$$

$$\left. \begin{array}{l} \tan\Psi = \sqrt{1 + a} / \sqrt{1 - a} \\ \sin(\Delta + 2P) = b / \sqrt{1 - a^2} \end{array} \right\} \quad (3)$$

In this case, the azimuth angle of the quarter-wave plate 3 is fixed to 45°. Then, if the variations or changes of the ellipsometric parameters $\Psi$ and $\Delta$ are obtained by putting P and A into P + $\delta P$ and A + $\delta A$, respectively, the coefficients for $\delta P$ and $\delta A$ in the equation (1) may be calculated. The coefficient for $\delta C$ may be obtained by putting the azimuth angle of the quarter-wave plate 3 to 45° + $\delta C$ when the equations (2) and (3) are derived and by obtaining the variations or changes of the ellipsometric parameters $\Psi$ and $\Delta$.

It will be described how the actual azimuth angle error is corrected.

The azimuth angles should be adjusted for the polarizer 2 and the quarter-wave plate 3 of the polarizer assembly and the analyzer 4 of the analyzer system, and the azimuth angles of the polarizer 2 and the quarter-wave plate 3 are relatively adjusted before the apparatus is assembled in the processor system. This may be executed similarly to the case of the conventional ellipsometer in which a polarizer assembly, an analyzer system and a sample holder are integrated. in case of assembling the apparatus in the processor system, the polarizer 2 and the quarter-wave plate 3 of the polarizer assembly can be integrally adjusted for the azimuth angles, and the azimuth angles of the integrated polarizer assembly and analyzer 4 may be adjusted to concur with the incidence plate, i.e., the plane including the incidence light and the reflected light, or the direction perpendicular to the plane by using the conventional azimuth angle adjusting method. In this case, the adjustment may be coarsely performed because the angles are finely corrected later, and thus the adjustment of the azimuth angles may be easily carried out as compared with the conventional case. Then, the scale of each of the azimuth angles is set to the corresponding angle. In this way, the coarsely setting of each azimuth angle are made.

The correction of the coarsely set azimuth angles will now be described.

Since the polarizer 2 and the quarter-wave plate 3 are integrally adjusted and the relative azimuth angle adjustment is initially performed, it is recognized that the relationship of $\delta P = \delta C$ is obtained and the relation (1) has a relation only to the $\delta P$ and the $\delta A$. Therefore, if the $\delta P$ and the $\delta A$ are evaluated, the ellipsometric parameters $\Psi'$ and $\Delta'$ determined by means of the equation (1) can be respectively corrected to the actual ellipsometric parameters $\Psi$ and $\Delta$. Then, to evaluate the $\delta P$ and the $\delta A$, the quarter-wave plate 3 is positioned with an azimuth angle which is read as 45°, and $\Delta'_0$, $\Psi'_{45}$, $\Delta'_{90}$ and $\Psi_{135}$ are determined by putting P=0°, 45°, 90° and 135°, respectively. That is, there is the following relationship:

$$\delta A = \frac{\tan2\Psi'}{4\cos\Delta'} \cdot (\Delta'_0 - \Delta'_{90}) \quad (4)$$

$$\delta P = -\frac{(\Psi'_{45} - \Psi'_{135}) - 2\cos\Delta' \cdot \delta A}{2\sin2\Psi'}$$

In this case, there is no significant difference even if the values of any of the cases of P=45° or 135° and 0° or 90° are to be used for the $\Psi'$ and $\Delta'$ not determined for the azimuth angles. Thus, the errors $\delta P$ and $\delta A$ are initially measured, and are corrected by means of the following equations using the relationship $\delta P = \delta C$ by the equation (1) in the subsequent measuring process.

$$\Psi = \Psi' + \sin2\Psi' \cdot \sin2P \cdot \delta P - \sin(\Delta' + 2P) \cdot \delta A \quad (5)$$

$$\Delta = \Delta' - \frac{2\cos(\Delta' + 2P)}{\tan2\Psi'} \cdot \delta A$$

Further, if measured when the quarter-wave plate is set with the azimuth angle 135°, the relation of the $\Delta$ of the equation (1) can be written as below with the measured value as $\Delta''$.

$$\Delta = \Delta'' + 2\delta P - 2\delta C - \frac{2\cos(\Delta'' + 2P)}{\tan2\Psi''} \cdot \delta A \quad (6)$$

Then, if $\Delta'$ and $\Delta''$ are measured in case of P =0°, it can be written as follows:

$$\Delta'_0 - \Delta''_0 \sim 2(\delta P - \delta C) \quad (7)$$

Therefore, the difference between the $\delta P$ and the $\delta C$ can be obtained by measuring the $\Psi'_0$ and the $\Psi''_0$. In this way, even if the relative azimuth angle adjustment of the polarizer 2 and the quarter-wave plate 3 is displaced before assembling the apparatus in the processor system, and thus there is $\delta P \neq \delta C$, such error can be exactly corrected by means of the equation (1).

Figure 2:
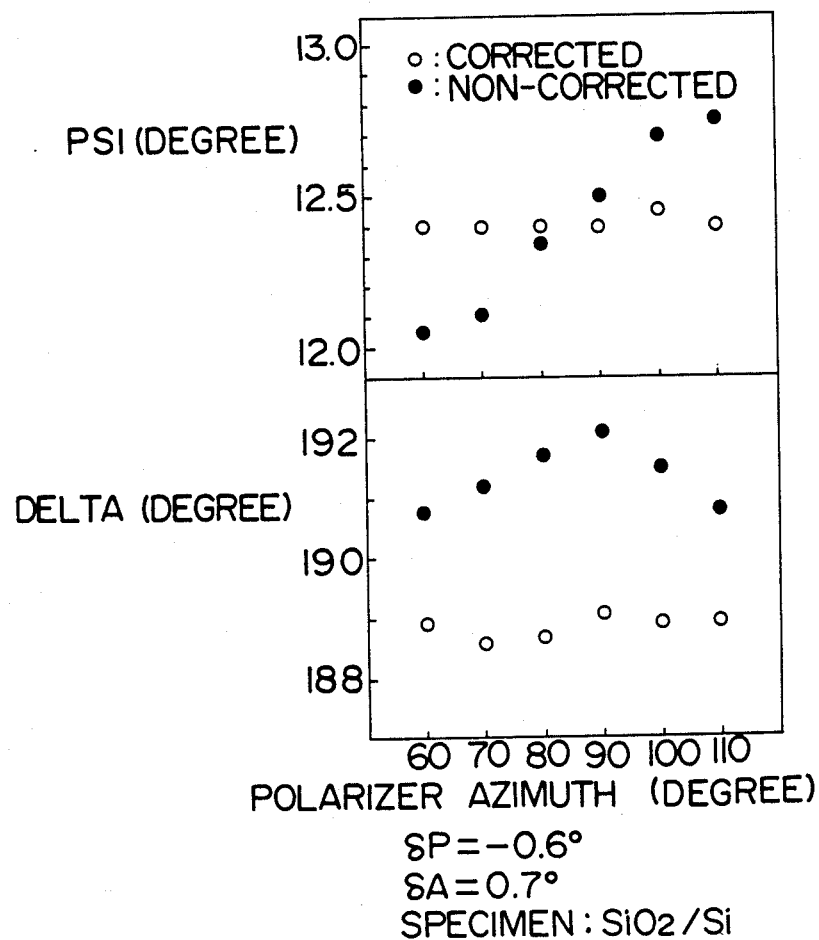
FIG. 2 is a graph showing the ellipsometric parameters obtained by the method of the present invention.

FIG. 2 shows the accurate ellipsometric parameters obtained by measuring the $\delta P$ and the $\delta A$ in accordance with the method of the present invention. The measured $\delta P$ and $\delta A$ were −0.60° and 0.70°, respectively in this case. As the result of the correction of the values $\Psi'$ and $\Delta'$ as measured (rounded by solid black circles) by means of the equation (1), it is appreciated that the ellipsometric parameters $\Psi$ and $\Delta$ (rounded by white circles) the increased in accuracy. This is because, if the values of the $\Psi$ and $\Delta$ are accurate with respect to the azimuth angle of the polarizer, they must be constant without variation.

According to the method of the present invention as described above, since the errors of the azimuth angles $\delta p$ and $\delta A$ are measured to obtain accurate ellipsometric parameters, when the ellipsometer apparatus is to be connected to the processor system, the azimuth angle can be simply determined, and even if it is displaced, accurate measurement can be performed without necessity of readjustment. Therefore, by utilizing the azimuth angle correcting method of the present invention, it is recognized that the ellipsometry can be easily utilized as an in-process monitor. There will be also expected an availability even in a thin film forming process which is necessary for higher accuracy.

What is claimed is:

1. A method of correcting the azimuth angle of a photometric ellipsometer having a light processing assembly including a polarizer subassembly forming a light source portion and an analyzer subassembly forming a light receiving portion, the polarizer subassembly included in light source, a polarizer and a quarter-wave plate and the analyzer subassembly including an analyzer and a photo-detector, the quarter-wave plate being disposed at an azimuth angle of 45° to the polarizer or analyzer subassembly, comprising the step of positioning the polarizer or analyzer subassembly with an azimuth angle by 45° each time, measuring ellipsometric parameters $\Psi'$ and $\Delta'$ and determining the errors $\delta A$ and $\delta P$ in the azimuth angle of the polarizer and the analyzer subassemblies respectively, and cancelling the determined error values $\delta A$ and $\delta P$ in the azimuth angles of the polarizer subassemblies and the analyzer subassemblies from the measured ellipsometric parameters $\Psi'$ and $\Delta'$ to obtain accurate ellipsometric parameters $\Psi$ and $\Delta$.

2. A method as claimed in claim 1, wherein the accurate ellipsometric parameters $\Psi$ and $\Delta$ are obtained by the following equation:

$$\Psi = \Psi' + \sin 2\Psi' \cdot \sin 2P \cdot \delta P - \sin(\Delta' + 2P) \cdot \delta A$$

$$\Delta = \Delta' - \frac{2\cos(\Delta' + 2P)}{\tan 2\Psi'} \cdot \delta A$$

wherein P is the azimuth angle of the polarizer or an analyzer and $\delta P$ and $\delta A$ are the errors in the azimuth angles of the polarizer or analyzer and the analyzer or polarizer, respectively.

3. A method of correcting the azimuth angle of a photometric ellipsometric as defined in claim 1, including the step of summing the values of the measured of the ellipsometric parameters $\Psi'$ and $\Delta'$ to cancel the errors in the azimuth angles of the polarizer subassembly and the analyzer subassembly thereby obtaining accurate elipsometomer parameters $\Psi$ and $\Delta$.

4. A method as claimed in claim 3, wherein the accurate ellipsometric parameters $\Psi$ and $\Delta$ are obtained by the following equation:

$$\Psi = \frac{\Psi'_{45} + \Psi'_{135}}{2}, \Delta = \frac{\Delta'_0 + \Delta'_{90}}{2}$$

when the azimuth angle P of the polarizer or analyzer is set to 0°, 45°, 90° and 135°.

* * * * *